United States Patent [19]

Graham et al.

[11] 4,134,214

[45] Jan. 16, 1979

[54] FREEZE-DRYING PROCESS FOR THE PREPARATION OF MENINGOCOCCUS VACCINE WITHOUT DEGRADATION OF POTENCY

[75] Inventors: Glen D. Graham, Rocky Hill; William A. Sklarz, Edison, both of N.J.

[73] Assignee: Merck & Co., Inc., Rahway, N.J.

[21] Appl. No.: 822,309

[22] Filed: Aug. 5, 1977

[51] Int. Cl.$^2$ .................................................. F26B 5/06
[52] U.S. Cl. ................................................ 34/5; 34/13; 34/15; 34/20; 424/88; 424/92
[58] Field of Search .................... 34/5, 13, 20, 15; 424/88, 93, 180, 92

[56] References Cited

U.S. PATENT DOCUMENTS

| 3,449,885 | 6/1969 | Starkey | 34/5 |
| 3,594,913 | 7/1971 | Tooby | 34/5 |
| 3,607,858 | 9/1971 | Querry | 34/5 |

FOREIGN PATENT DOCUMENTS 1055841  2/1954  France ............................................. 34/5

OTHER PUBLICATIONS

Benedict et al., Appl. Microbiol, vol. 6, 1958, pp. 401–407.

*Primary Examiner*—Leland A. Sebastian
*Attorney, Agent, or Firm*—Donald J. Perrella; Edmunde D. Riedl; Julian S. Levitt

[57] ABSTRACT

The purified Group A polysaccharide antigen isolated from *N. meningitidis* for vaccination against this type of bacterial meningitidis is prepared from an isotonic ratio of aqueous sodium chloride solution freeze-dried at temperatures of from −20° C. to −30° C. This low temperature lyophilization dries the sodium chloride polysaccharide menstrum without loss of molecular weight, i.e., potency.

5 Claims, No Drawings

FREEZE-DRYING PROCESS FOR THE PREPARATION OF MENINGOCOCCUS VACCINE WITHOUT DEGRADATION OF POTENCY

DISCLOSURE OF THE INVENTION

This invention relates to the lyophilization of freeze-drying of polysaccharides derived from Group A meningococcus. More particularly, this relates to freeze-drying of Group A at a temperature range found to be critical which is from −20° C to −30° C.

Meningococcal meningitis is a disease involving inflammation of the membranes enveloping the brain and spinal cord. In the past, most cases of bacterial meningitis were acute and fatal. The subsequent introduction of antibiotic therapy reduced the mortality rate for cases recognized early in their course. Nonetheless, undiagnosed meningitis remains a morbid disease. Even with antibiotic administration the prognosis is poor especially for the younger patient. This negative prognosis results in part because infants of three months to two years of age rarely manifest typical symptoms of the disease. Thus, antibiotic therapy which must be initiated early is often delayed until the infant is desperately and obviously ill or the presence of the disease is confirmed by laboratory findings.

Meningococcal meningitis is caused by infection by the species *Neisseria meningitides.* This species is classified into serological groups; A, B, C and D etc. Each of these groups is classified by a characteristic capsular polysaccharide associated with the cell wall of that particular group. It was discovered that this cell component comprised of polysaccharide when introduced into a mammal will induce antibiody production; hence, protection against later infection. Such vaccines can be isolated from whole culture and administered by known techniques.

We have now discovered a process for preparing meningococcal polysaccharide vaccines that employs freeze-drying step for preservation of the vaccine product that does not degrade molecular weight. This is advantageous because it is well accepted that higher molecular weight polysaccharide products achieve a greater level of immunogencity as compared to lower molecular weight material.

This antigenicity or potency of bacterial meningitidis vaccines as a function of molecular weight is encountered with Group A and Group C polysaccharide. The polysaccharide material used for meningitidis vaccine upon isolation and purification is very unstable and to preserve its potency it, like other biologicals, is freeze-dried. It is already known, as exemplarily described in French Pat. No. 1,055,841 and U.S. Pat. No. 3,271,875 to stabilize substances in an aqueous environment by a process called lyophilization, consisting in solidifying the aqueous environment by freezing and eliminated subsequently the ice by selective sublimation under a vacuum. The freeze-dried or lyophilized material is most stable at 0° C. or less and may be stored at those temperatures for relatively extended periods.

However, while freeze-drying of the polysaccharide is more efficient at temperatures of in excess of −20° C., we have found that these more efficient temperatures in terms of drying time result in an apparent drop in molecular weight. This drop is not a degradation in which bonds are broken, but rather appears to be conformational change in which monomers are enclosed in a smaller volume, thus, giving the molecule a smaller apparent size. Further, it was discovered that the association of water molecules with the polysaccharide are essential to maintaining the polymer conformation.

By the process specified herein, it is possible to dry the isotonic menstrum to below a moisture content of less than 3% by lyophilization without dehydrating the polysaccharide and incurring a subsequent molecular weight decrease. This is accomplished by maintaining the temperature of the material being lyophilized to a temperature of −30° C. to −20° C. for the duration of the lyophilization. By use of this reduced temperature, the free water (ice) is sublimed away from the salt menstrum while bound water, being more tightly associated with the polysaccharide at reduced temperature is not volatilized. The preferred mode involves lyophilization of a 0.15 to 0.35 cm. depth of a sterile solution containing 1.47 mg./ml. meningococcal Group A polysaccharide and 1.25% w/v sodium chloride.

In carrying out the procedure of the invention, conveniently sized aliquot portions of the polysaccharide vaccine either Group A, Group C or a mixture of Group A and Group C is asceptically dispensed into suitable vials. The vials of solution are frozen at −40° C. and allowed to age at this temperature on the shelf of a tray freeze drier. This aging step carried out prior to the actual lyophilization is not essential to the practice of the invention. However, it is an advisable and even preferred practice so as to avoid obtaining a super-cooled liquid during the remainder of the lyophilization procedure.

A vacuum of less than 500 microns mercury is established in the freeze-drying apparatus chamber. While this pressure is satisfactory, it is preferred that a vacuum of less than 200 microns of mercury be attained prior to raising the temperature to much above −40° C.

It should be understood that the isotonic polysaccharide material can be placed in a freeze-drying apparatus at a temperature of −30° C. to −20° C. and a pressure of less than 500 microns of mercury and good results be obtained. However, it is much preferred to employ the prior temperature equilibration step to bring the material to be lyophilized to a temperature of less than −30° C. and also a vacuum of less than 200 microns of mercury is much preferred. The shelf temperature of the freeze-drying apparatus is raised to a maximum of −30° C. and held constant until the temperature as indicated by the thermocouples imbedded in subliming ice read a constant value for in excess of two hours. The vacuum chamber is then vented with a sterile gas, preferably dry argon, and the vials containing the now lyophilized vaccine are stoppered. A dry (less than 1% moisture) fully active freeze-dried product results.

For the lyophilization of mixed meningitidis vaccine 10 and 50 dose sizes of vaccine the sterile solution contains 1.47 mg./ml. meningococcal Type A polysaccharide, 1.47 mg./ml. meningococcal Type C polysaccharide in 12.5% w/v sodium chloride. The freeze-drying procedure remains the same. In the case of single dose the sterile solution contains 0.100 mg./ml. meningococcal polysaccharide in 0.9% sodium chloride. The lyophilization cycle remains the same.

The following examples will serve to illustrate the invention.

EXAMPLE 1

2.2 ml. of a sterile aqueous solution containing 1.47 mg./ml. Group A meningococcal polysaccharide and 12.5% w/v sodium chloride are dispensed in each of fifty 12.5 inch diameter vials. The vials are only partially stoppered with fluted stoppers to allow vapor flow.

The vials are then frozen at −40° C. in a tray freezer until the lyophilization step. The vials, placed on −40° C. shelf of a 16 square foot tray freeze drier, are held at atmospheric pressure. A vacuum of less than 100 microns mercury is established while the shelf temperature is linearly increased to −30° C. over a period of three hours and maintained at the −30° C. temperature for 46 hours. The vaccine product is found to be equilibrated with shelf temperature after 36 hours. The final vacuum is 23 microns of Hg.

The vacuum chamber is then vented with sterile argon and the vials stoppered. A moisture content of 0.25% measured against $P_2O_5$ is obtained. Molecular weight, measured by obtaining a partition coefficient for sepharose gel chromatography, is found to have a value Kd=0.10. This represents less than a 0.05 rise in the Kd value.

EXAMPLE 2

Aliquots of 0.44 ml. of a sterile aqueous solution containing 1.47 mg./ml. Group A meningococcal polysaccharide and 12.5% w/v sodium chloride are dispensed into each of 3744 10 dose vials.

Partially stoppered vials are stored at −40° C. for about 12 hours. The vials are then placed on a −40° C. shelf of an eight foot tray freeze drier and held at −40° C. for one hour at atmospheric pressure. A vacuum of less than 100 microns is established, and the shelf temperature is then linearly raised to −30° C. over a three hour period and maintained for 24 hours. Vaccine product temperature equilibrated with the shelf temperature after a 15 hour period. The final vacuum reading was 17 microns of Hg.

Moisture content of product is 0.37% and has a chromatography partition coefficient of 0.22.

EXAMPLE 3

Aliquot portions of 0.5 ml. of a sterile solution containing 10 gm. meningococcal Group A polysaccharide and 0.9% sodium chloride are dispensed into each of 92,400 single dose vials.

Partially stoppered vials are stored at −40° C. until lyophilization. Vials are then placed on a −40° C. shelf of a 170 foot 2 tray freeze-drier and held at −40° C. for one hour. A vacuum of less than 100 microns is established and shelf temperature linearly raised to −30° C. over a three-hour period. This shelf temperature is maintained for 46 hours. Temperature of the shelf and product is equilibrated after 36 hours. Final vacuum is 28 microns.

Moisture of the dried product is 0.6%. A partition coefficient of Kd=0.29 is obtained indicating an increase of less than 0.10 for the product.

EXAMPLE 4

Aliquot portions of 2.2 ml. of a sterile 1.47 mg./ml. meningococcal Group A polysaccharide is dispensed into 50 dose (1.25 inch diameter) vials. Vials are frozen at −40° C., and placed on a −40° C. shelf of a tray freeze-drier. The shelf temperature is raised to 1° C. linearly over a five-hour period, and maintained for 15 hours. Resulting product has a moisture content of 0.51% moisture and a chromatographic partition coefficient of Kd=0.41, indicating a less than 0.05 rise.

As seen from the above examples, the end point is reached after the moisture content is reduced below 3% and preferably below 1%. Generally, this is achieved after from 15 to 48 hours at the specified temperatures and pressures.

What is claimed is:

1. An improved process for preserving vaccine derived from Group A and Group C polysaccharides of *N. meningitidis* wherein the molecular weight is not degraded which improvement comprises lyophilizing an isotonic solution of said polysaccharide which is maintained at a temperature of from −20° C. to −30° C. until the moisture content is less than 3%.

2. A process according to claim 1 where the lyophilization is continued until the moisture content is less than 1%.

3. A process according to claim 1 where the lyophilization process is conducted at a pressure of less than 500 microns of mercury.

4. A process according to claim 1 where the lyophilization process is conducted at a pressure of less than 200 microns of mercury.

5. A process according to claim 1 where prior to lyophilization the polysaccharide is cooled to a depressed temperature of −30° C. to −40° C. and maintained within that temperature range for a period of at least 12 hours, and said lyophilization step commenced while said polysaccharide is at said depressed temperature.

* * * * *